United States Patent [19]

Gebert et al.

[11] 4,235,899
[45] Nov. 25, 1980

[54] SUBSTITUTED O-(2-HYDROXYPROPYL)-ALDOXIMES

[75] Inventors: Ulrich Gebert, Kelkheim; Wolfgang Raether, Dreieichenhain, both of Fed. Rep. of Germany

[73] Assignee: Hoechst Aktiengesellschaft, Frankfurt, Fed. Rep. of Germany

[21] Appl. No.: 849,936

[22] Filed: Nov. 9, 1977

[30] Foreign Application Priority Data

Nov. 9, 1976 [DE] Fed. Rep. of Germany ....... 2651084

[51] Int. Cl.³ .................. C07D 403/12; C07D 405/12; C07D 407/12; C07D 413/12

[52] U.S. Cl. ..................................... 424/246; 424/244; 424/248.56; 424/248.57; 424/250; 424/274; 424/273 R; 424/285; 424/267; 542/406; 542/407; 260/347.7; 548/339

[58] Field of Search .................. 542/406, 416, 407; 548/339; 260/347.7; 424/244, 246, 248.56, 248.57, 250, 274, 273 R, 285, 267

[56] References Cited

U.S. PATENT DOCUMENTS

| | | | |
|---|---|---|---|
| 3,184,452 | 5/1965 | Druey et al. .................. | 260/347.7 X |
| 3,583,985 | 6/1971 | Bambury et al. ............... | 548/339 X |
| 3,836,528 | 9/1974 | Minami et al. ................. | 260/347.7 X |
| 3,951,963 | 4/1976 | Winkelmann et al. .............. | 542/406 |

Primary Examiner—Arthur P. Demers

Attorney, Agent, or Firm—Quaintance, Murphy & Richardson

[57] ABSTRACT

Compounds of general formula

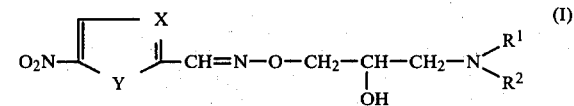

wherein X represents a methine group and Y is an oxygen atom, or X represents a nitrogen atom and Y the group $NR^3$ in which $R^3$ represents a radical selected from the group consisting of a hydrogen atom, a methyl, ethyl and hydroxyethyl group; and $R^1$ and $R^2$ each represent a radical of the group hydrogen atom, an alkyl and hydroxyalkyl group each containing up to 6 carbon atoms, or an aryl group containing up to 10 carbon atoms; and $R^1$ and $R^2$, together with the nitrogen atom to which they are attached, form a 5- to 7-membered saturated ring which contains not more than one further, heterocyclic atom selected from the group consisting of oxygen, sulphur and nitrogen and being unsubstituted or substituted by one of the groups an alkyl and hydroxyalkyl group each containing up to 6 carbon atoms and an aryl group containing up to 10 carbon atoms and physiologically acceptable acid addition salts thereof and a pharmaceutical composition containing them.

6 Claims, 13 Drawing Figures

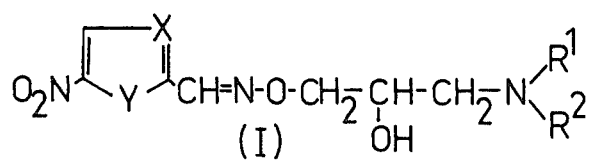
(I)
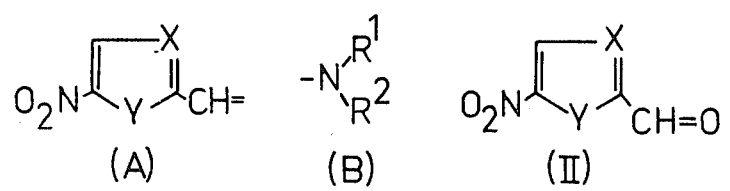
(A) (B) (II)
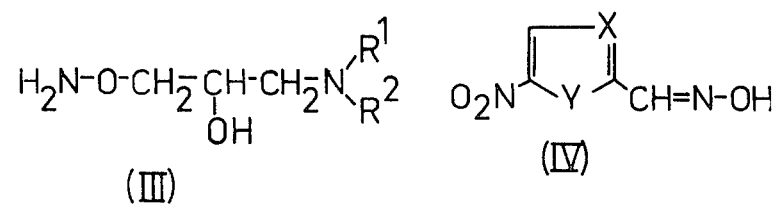
(III) (IV)
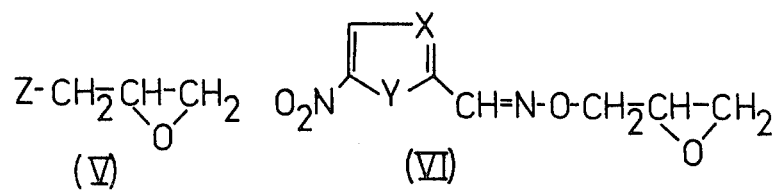
(V) (VI)
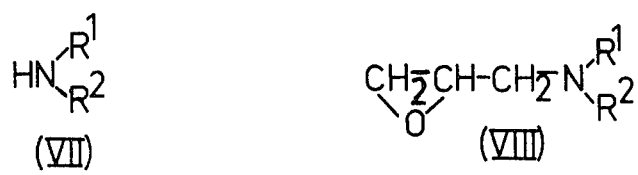
(VII) (VIII)
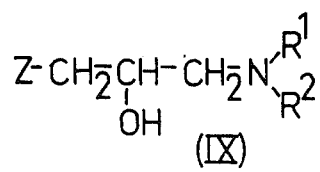
(IX)

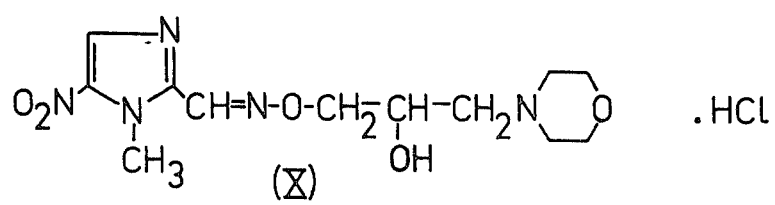
(X)
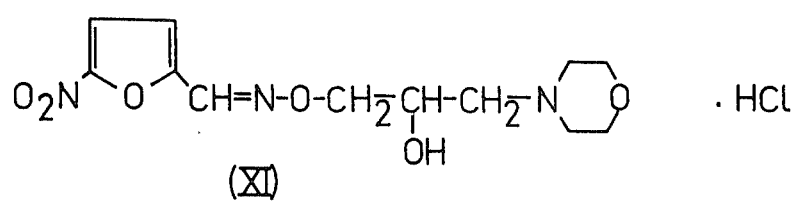
(XI)
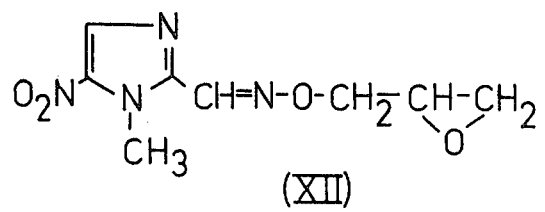
(XII)
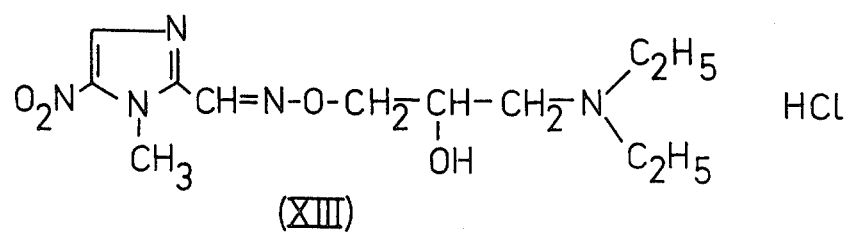
(XIII)

SUBSTITUTED O-(2-HYDROXYPROPYL)-ALDOXIMES

This invention relates to substituted O-(2-hydroxypropyl)-aldoximes having interesting pharmacological properties.

Up to the present, 1-(2-hydroxyethyl)-2-methyl-5-nitroimidazole (metronidazole) is the standard drug for the treatment of protozoic diseases especially trichomoniasis. Furthermore, 1-alkyl-5-nitro-2-imidazolaldoximes and alkyl ethers thereof have been described as active substances against protozoa.

A large number of nitrofuran derivatives having antibacterial and fungistatic activity is also known. Activity against protozoa is, however, reported only more rarely. Thus, although 5-nitro-2-furaldoxime (nifuroxime) shows good trichomonacidal activity on topical application, systemic activity is lacking. The term "systemic activity" means that the substance can be detected after oral or parenteral administration in various organs by, for example, fluorescence measurements or colorimetric measurements, and is active in those organs.

According to one aspect of the present invention there are provided compounds of general formula

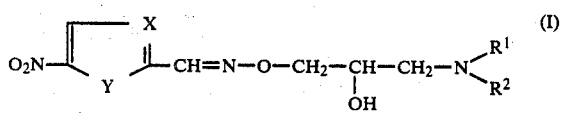

[wherein X represents a methine group and Y an oxygen atom, or X represents a nitrogen atom and Y the group $>NR^3$ (in which $R^3$ represents a hydrogen atom or a methyl, ethyl or hydroxyethyl group); and $R^1$ and $R^2$, which may be the same or different, each represents a hydrogen atom, an alkyl or hydroxyalkyl group containing up to 6 carbon atoms, or an aryl group containing up to 10 carbon atoms; or $R^1$ and $R^2$, together with the nitrogen atom to which they are attached, form a 5- to 7-membered saturated ring optionally interrupted by not more than one oxygen, sulphur or further nitrogen atom, and optionally substituted by an alkyl or hydroxyalkyl group containing up to 6 carbon atoms, or by an aryl group containing up to 10 carbon atoms] and physiologically acceptable acid addition salts thereof.

When $R^1$ and/or $R^2$ in the compounds according to the invention represent alkyl or hydroxyalkyl groups, or together with the nitrogen atom to which they are attached, form a ring substituted by alkyl or hydroxyalkyl groups, these groups preferably contain up to 4 carbon atoms. Similarly when $R^1$ and/or $R^2$ represent aryl groups or a ring substituted by aryl groups, these groups preferably contain up to 6 carbon atoms, and advantageously represent a phenyl group.

Preferred compounds according to the invention are those in which at most one of $R^1$ and $R^2$ is hydrogen, and also compounds in which $R^1$ and $R^2$ together contain a total of from 4 to 10 carbon atoms, especially 4 to 8 carbon atoms, and additionally those compounds in which neither of $R^1$ and $R^2$ represents hydrogen. If $R^1$ and $R^2$ together form a cyclic group, this can also contain a further heteroatom in these preferred compounds and any substitutents on the ring preferably contain a total of not more than 12 carbon atoms.

When $R^1$ and $R^2$, together with the nitrogen atom to which they are attached, in the compounds according to the invention represent a 5- to 7-membered ring, this ring is, for example, an optionally substituted pyrrolidinyl, piperidyl, morpholinyl, hexamethyleniminyl, thiamorpholinyl, tetrahydro-1,4-thiazin-1,1-dioxide or piperazinyl group and preferably an optionally substituted 1-piperazinyl group group or a 2,5-dialkylpyrrolidinyl, 2,6-dialkylpiperidyl or 2,2,6,6-tetraalkylpiperidyl group.

As indicated above the compounds according to the invention possess interesting pharmacological properties. In particular they exhibit good systemic activity against protozoa (such as trichomonas), amoeba and trypanosomes. Tests on compounds according to the invention which we have effected, indicate that their trichomonacidal activity is superior to the known 5-nitroimidazoles and nitrofurans mentioned above. We have found that the trypanocidal activity of the compounds of the invention is more pronounced with nitrofuran aldoximes than with the corresponding nitroimidazole compounds. The nitrofuran compounds have also shown a degree of antifungal and antibacterial activity. Compounds of formula I according to the invention which we have investigated have shown an excellent in vitro activity against *Trichomonas vaginalis* and *Entamoeba histolytica*.

Preferred compounds according to the invention by virtue of their favourable pharmacological properties are:

O-[3-(4-Morpholinyl)-2-hydroxypropyl]-1-methyl-5-nitro-2-imidazolaldoxime and physiologically acceptable acid addition salts thereof;

O-(3-hexamethyleneimino-2-hydroxypropyl)-1-methyl-5-nitro-2-imidazolaldoxime and physiologically acceptable acid addition salts thereof;

O-[3-(2,5-dimethyl-1-pyrrolidinyl)-2-hydroxypropyl]-1-methyl-5-nitro-2-imidazolaldoxime and physiologically acceptable acid addition salts thereof;

O-[3-(2,6-dimethyl-piperidyl)-2-hydroxypropyl)-1-methyl-5-nitro-2-imidazolaldoxime and physiologically acceptable acid addition salts thereof;

and especially the hydrochloride salts thereof.

In general, compounds of general formula I may be prepared by linking the structural grouping

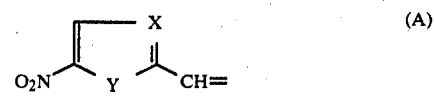

with the grouping

via the bridging grouping

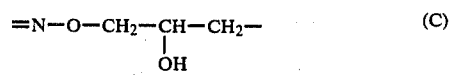

Thus, according to further aspects of the present invention, there are provided the following processes for the preparation of compounds of general formula I:

(a) reacting an aldehyde of formula

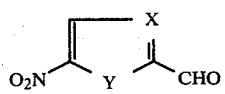 (II)

(in which X and Y are hereinbefore defined) or a reactive derivative thereof, with a compound of formula

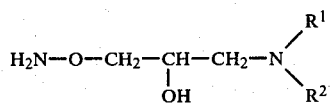 (III)

(in which $R^1$ and $R^2$ are as hereinbefore defined) or an acid addition salt thereof;

(b) reacting a compound of formula

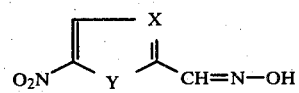 (IV)

(wherein X and Y are as hereinbefore defined) with (b1) an alkylating agent in the form of a 2,3-epoxypropyl compound of formula

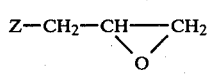 (V)

(wherein Z is a halogen atom, preferably a chlorine or bromine atom, or a reactive sulphonic acid ester group) to form a compound in the presence of an acid binding agent of formula

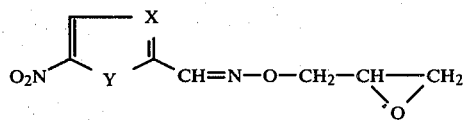 (VI)

(wherein X and Y are as hereinbefore defined), and subsequently aminolytically opening the oxirane ring thereof by reaction with a compound of formula

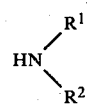 (VII)

(wherein $R^1$ and $R^2$ are as hereinbefore defined);

(b2) an alkylating agent in the form of a basically substituted epoxypropyl compound of formula

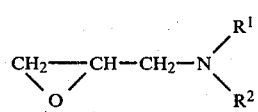 (VIII)

(wherein $R^1$ and $R^2$ are as hereinbefore defined); or (b3) an alkylating agent in the form of an aminoalcohol of formula

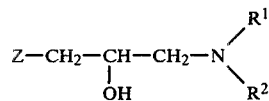 (IX)

(wherein $R^1$, $R^2$ and Z are as hereinbefore defined) preferably in the presence of an acid binding agent.

If desired, free bases of the compounds of general formula I produced by any of the above processes may be converted to the corresponding acid addition salts thereof by known processes.

Reactive derivatives of compounds of formula II for use in process (a) may be, for example, their hemi- or full acetals, mercaptals, aminals and acylals. Similarly, aldimines, other oximes, hydrazones, semicarbazones, thiosemicarbazones, cyanohydrins or bisulphite addition compounds may also be used as starting compounds.

Starting compounds of formula III for use in process (a) may be, for example, O-(3-tert.-butylamino-2-hydroxypropyl)-hydroxylamine, O-(3-diethylamino-2-hydroxypropyl)-hydroxylamine, O-(3-dibutylamino-2-hydroxypropyl)-hydroxylamine, O-[3-di-(2-hydroxyethyl)amino-2-hydroxypropyl]-hydroxylamine, O-[3-N-methyl-N-phenylamino)-2-hydroxypropyl]-hydroxylamine O-[3-(1-pyrrolidinyl)-2-hydroxypropyl]-hydroxylamine, O-(3-piperidyl-2-hydroxypropyl)-hydroxylamine, O-[3-(4-morpholinyl)-2-hydroxypropyl]-hydroxylamine, O-(3-hexamethyleneimino-2-hydroxypropyl)-hydroxylamine, O-[3-(2,5-dimethyl-1-pyrrolidinyl)-2-hydroxypropyl]-hydroxylamine, O-[3-(2,6-dimethyl-1-piperidyl)-2-hydroxypropyl]-hydroxylamine O-[3-(2,2,6,6-tetramethyl-1-piperidyl)-2-hydroxypropyl]-hydroxylamine, O-[3-(4-methyl-1-piperazinyl)-2-hydroxypropyl]-hydroxylamine, O-{3-[4-(2-hydroxyethyl)-1-piperazinyl]-2-hydroxypropyl}-hydroxylamine and O-[3-(4-phenyl-1-piperazinyl)-2-hydroxypropyl]-hydroxylamine.

Starting compounds of formula IV for use in process (b) may be, for example, 1-methyl-, 1-ethyl- and 1-(2-hydroxyethyl)-derivatives of 5-nitro-2-imidazol-aldoxime and 5-nitro-2-furaldoxime.

Preferred compounds of formula V for use in process (b1) are, for example, epichlorohydrin, epibromohydrin, 2,3-epoxypropyl-benzene sulphonate, -p-toluene sulphonate or -methane sulphonate.

Amines of formula VII for use in process (b1) may be, for example, primary amines, such as methyl-, ethyl-, propyl-, isopropyl-, butyl-, isobutyl- and tert.-butylamine, and also the various monopentyl and monohexylamines, aniline and secondary amines corresponding to the above primary amines, such as, for example, dimethylamine and other dialkylamines containing up to 6, preferably up to 4 carbon atoms in the alkyl groups, N-methylaniline or alkanolamines such as, for example, diethanolamine. Cyclic amines which may also be used are compounds, such as pyrrolidine, piperidine, hexamethyleneimine, 2,5-dimethylpyrrolidine, 2,6-dimethylpiperidine, 2,2,6,6-tetramethylpiperidine or other heterocyclic compounds containing, in addition to the nitrogen atom, an oxygen, sulphur or further nitrogen atom advantageously separated by at least two carbon atoms from the nitrogen atom of the compound of formula VII, such as, for example, morpholine, thiamorpholine, tetrahydro-1,4-thiazin-1,1-dioxide, piperazine and homopiperazine, optionally substituted in the 4-position by a $(C_1-C_4)$-alkyl, hydroxy-$(C_1-C_4)$-alkyl or phenyl group, such as, for example, 4-methylpiperazine, 4-(2-hydroxyethyl)-piperazine, and 4-phenylpiperazine Cyclic compounds may also have more than one substitutent, e.g. up to 4 methyl and/or ethyl substituents, the substituents together having generally not more than 12, preferably not more than 8 carbon atoms.

The processes according to the invention are conveniently carried out in a solvent or dispersion agent. In process (a) equimolar quantities of the starting materials are preferably used in a solvent comprising an aqueous-alcohol.

Alkylation of compounds of formula IV according to process (b) may if desired be effected in solvents comprising, for example, anhydrous alcohols, hydrocarbons, aprotic solvents or an excess of the alkylating agent, and preferably in the presence of a base such as alkali metal or alkaline-earth metal hydroxides, carbonates, hydrides or alcoholates or in the presence of separately prepared alkali metal or alkaline-earth metal oximates. Aminolysis of the compounds of formula VI in process (b1) is advantageously carried out in an inert solvent, such as for example, an alcohol, hydrocarbon or aprotic solvent.

Alcohols which may be used as solvents are, for example, methanol, ethanol, propanol, isopropanol, butanol and isobutanol and suitable hydrocarbon solvents are, for example, hexane, cyclohexane, benzene, toluene or xylene. Suitable aprotic solvents are, for example, dimethylformamide, dimethylacetamide, N-methylpyrrolidone, tetramethylurea, hexamethylphosphoric trisamide and dimethylsulphoxide.

If desired, the processes can be carried out under elevated or reduced pressure, though it is preferred to work under atmospheric pressure. Reaction temperatures for the processes may be between 0° C. and the boiling point of the reaction mixture at the selected pressure, depending on the particular reaction effected. When effected in alcoholic media the processes are preferably carried out at atmospheric pressure generally at temperatures between 20° and 100° C., and when using aprotic solvents generally at temperatures from 60° to 130° C., preferably about 100° C. Reaction times may vary between a few minutes and a few hours, depending on the particular process used.

As stated above the products of the processes are generally the free bases of compounds of formula I and may, if desired, be converted into physiologically acceptable salts thereof. Acids which may be used for the preparation of physiologically acceptable salts are, for example, halogen hydracids (especially hydrochloric acid), sulphuric acid, phosphoric acid, tartaric acid, maleic acid, fumaric acid and acetic acid.

As stated above, compounds of general formula I are active against protozoic diseases in humans and animals, especially diseases caused by, for example, infection with *Trichomonas vaginalis, Entamoeba histolytica* and various trypanosomic organisms.

Thus, according to a further aspect of the present invention, there are provided pharmaceutical compositions comprising as active ingredient at least one compound of general formula I (as hereinbefore defined) or a physiologically acceptable acid addition salt thereof in association with a pharmaceutical carrier or excipient. The compositions according to the invention may be conveniently in a form suitable for oral, rectal, parenteral, topical or vaginal administration. Thus, for oral administration, compositions in the form of tablets or capsules may be used. Depending on the activity of the particular active ingredient used, the compositions may be administered in daily amounts of, for example, 100 to 750 mg, preferably 200 to 500 mg of the active ingredient. The compositions are desirably in the form of dosage units. The may also contain conventional pharmaceutical carriers or excipients.

The active ingredient is preferably administered on several, e.g. 5 to 10, successive days or, alternatively as a single dose of 1000 to 2000 mg.

It is possible, however to administer the active ingredient in the form of micro-capsules without the addition of pharmaceutical carriers or excipients.

Other convenient forms of administration of the compositions of the invention include gels, creams, ointments, suppositories, pessaries, solutions and forms adapted to provide a sustained release of the active ingredient.

In vitro and in vivo tests which we have effected on the compounds of the invention have indicated that they are distinguished by having a good compatibility and a reliable activity, especially against trichomonas, and may be superior to the known comparative drugs metronidazole, 1-methyl-5-nitro-2-imidazolaldoxime and nifuroxime. Some of these tests are hereinafter described:

Effects against Trichomonas foetus—Test: in vivo

The test for activity against *Trichomonas foetus* was conducted on albino mice (NMRI) of both sexes from a breeding colony. The body weight of the animals was between 10 and 12 g. The test substances were administered in two equal individual doses orally with a pharyngeal probe either in aqueous solution or, in the case of those compounds which dissolve in water with difficulty, as a methyl cellulose suspension. The first dose was administered 2 hours before and the second dose 2 hours after intraperitoneal infection with 19 millions of organisms/animal, suspended in 0.5 ml of "Culture medium Merck I" (Merck AG, Darmstadt, Germany). The groups to which the substances were administered comprised 4 or 5 animals per test substance and dosage. As an infection control group, 10 infected, but untreated, mice were used in each test. A further group of 5 animals which were neither infected nor treated served as a blank control. 6 days after infection all the test animals were killed and the organism count in the peritoneal exudate of the animals treated with the compounds of the invention and the known comparative drugs, was assessed by comparison with that of the untreated infection control group according to the following criteria:

Inactive:

Organism count in relation to infection control not significantly reduced.

Evaluation Number: 3-4.

Active:

(a) Indicated: Organism count in relation to infection control moderately reduced. Evaluation Number: 2.

(b) Unsatisfactory: Organism count in relation to infection control clearly lowered. Evaluation Number: 1.

(c) Good: No organism detectable. Evaluation Number 0.

In the following table "+" means that the animal died before the end of the test.

TABLE

| COMPOUND OF EXAMPLE | DOSE mg/kg p.o. | ORGANISM COUNT (T. foetus) in 4 or 5 animals | | | | |
|---|---|---|---|---|---|---|
| 1 | 2 × 25 | 0 | 0 | 0 | 0 | 0 |
|   | 2 × 20 | 0 | 0 | 0 | 0 | 0 |
|   | 2 × 15 | 0 | 0 | 0 | 0 | 0 |
|   | 2 × 12.5 | 0 | 0 | 0 | 0 | 0 |
| 3 | 2 × 50 | 0 | 0 | 0 | 0 |  |
|   | 2 × 25 | 0 | 0 | 0 | 0 |  |
|   | 2 × 12.5 | 2 | 2 | 2 | 3 |  |
| 4 | 2 × 50 | 0 | 0 | 0 | 0 |  |
|   | 2 × 25 | 0 | 0 | 0 | 0 |  |
|   | 2 × 12.5 | 2 | 2 | 2 | 3 |  |
| 5 | 2 × 50 | 0 | 0 | 0 | 0 |  |
|   | 2 × 25 | 0 | 0 | 0 | 0 |  |
|   | 2 × 12.5 | + | 2 | 2 | 4 |  |
| 12 | 2 × 50 | 0 | 0 | 0 | 0 | 0 |
|   | 2 × 40 | 0 | 0 | 0 | 0 | 0 |
|   | 2 × 30 | 0 | 0 | 0 | 0 | 0 |
|   | 2 × 25 | 0 | 3 | 0 | 0 | 0 |
| 13 | 2 × 50 | 0 | 0 | 0 | 0 |  |
|   | 2 × 25 | 0 | 0 | 0 | 0 |  |
|   | 2 × 12.5 | 0 | 0 | 0 | 0 |  |
|   | 2 × 6.25 | 1 | 2 | 2 | 3 |  |
| 14 | 2 × 50 | 0 | 0 | 0 | 0 |  |
|   | 2 × 30 | 0 | 0 | 0 | 0 |  |
|   | 2 × 25 | 0 | 0 | 0 | 0 |  |
|   | 2 × 20 | 3 | 2 | 3 | 3 |  |
| 15 | 2 × 50 | 0 | 0 | 0 | 0 |  |
|   | 2 × 25 | 0 | 0 | 0 | 0 |  |
|   | 2 × 12.5 | 0 | 0 | 0 | 2 |  |
| 16 | 2 × 50 | 0 | 0 | 0 | 0 |  |
|   | 2 × 25 | 0 | 0 | 0 | 0 |  |
|   | 2 × 12.5 | 0 | 0 | 0 | 2 |  |
| metronidazole (Comparison) | 2 × 50 | 0 | 0 | 0 | 0 |  |
|   | 2 × 25 | 0 | 2 | 0 | 1 |  |
|   | 2 × 12.5 | 4 | 4 | 4 | 4 |  |
| 1-Methyl-5-nitro-2-imidazol-aldoxime (Comparison) | 2 × 150 | 2 | 3 | 4 | 4 |  |
|   | 2 × 100 | 4 | 4 | 4 | 4 |  |
| nifuroxime (Comparison) | 2 × 50 | 4 | 4 | 4 | + | 3 |
|   | 2 × 25 | 4 | 4 | 4 | 4 | 4 |
| Infection Control | — | 4 | 4 | 4 | 4 |  |

For a comparison of activity with nifuroxime (which does not exhibit a systemic activity), the following nitrofuran derivatives according to the invention were also tested

| | | | | | | |
|---|---|---|---|---|---|---|
| 2 | 2 × 50 | 0 | 0 | 0 | 0 | 0 |
|   | 2 × 25 | 4 | 0 | 0 | 1 | 3 |
|   | 2 × 12.5 | 4 | 3 | 3 | 3 | 3 |
| 6 | 2 × 75 | 0 | 0 | 0 | 0 |  |
|   | 2 × 50 | 0 | 0 | 0 | 0 |  |
|   | 2 × 25 | 2 | 0 | 0 | 3 |  |
|   | 2 × 12.5 | 3 | 3 | 3 | 3 |  |
| 17 | 2 × 50 | 0 | 0 | 0 | 0 | 0 |
|   | 2 × 40 | 0 | 0 | 0 | 0 | 0 |
|   | 2 × 30 | 0 | 0 | 0 | 0 | 3 |
|   | 2 × 25 | 3 | 2 | 2 | 2 | 1 |
| 23 | 2 × 50 | 0 | 0 | 0 | 0 | 0 |
|   | 2 × 40 | 0 | 0 | 0 | 0 | 0 |
|   | 2 × 30 | 0 | 0 | 0 | 0 |  |
|   | 2 × 25 | 0 | 2 | 1 | 3 | 0 |
|   | 2 × 12.5 | 3 | 2 | 3 | 2 | 2 |

We have also been able to demonstrate for the compounds of the invention tested, an in vitro activity against *Trichomonas vaginalis* amd *Entamoeba histolytica* which was superior to metronidazole. Thus, for example, for the compound of Example 10, the concentration required for complete destruction of *Trichomonas viginalis* organisms was 0.15 γ/ml, whereas for the comparative compound metronidazole it was 2.5 to 5.0 γ/ml. The corresponding inhibiting limit for *Entamoeba histolytica* is, for example, for the compound of Example 7 about 1.25 γ/ml, whereas the comparative drug is only active at 5 γ/ml.

The following Examples serve to illustrate the preparation of compounds according to the invention:

EXAMPLE 1

0-[3-(4-morpholinyl)-2-hydroxypropyl]-1-methyl-5-nitro-2-imidazolaldoxime hydrochloride (of formula X) according to process (a)

4.65 g (0.03 mol) of 2-formyl-1-methyl-5-nitroimidazole are dissolved warm in 50 ml of ethanol. After the addition of 7.5 g (0.03 mol) of 0-[3-(4-morpholinyl)-2-hydroxypropyl]-hydroxylamine dihydrochloride in 15 ml of water at approximately 40° C., a solution of 3.2 g (0.03 mol) of soda in 15 ml of water is added dropwise with continuous stirring. The mixture is subsequently stirred for 4 hours at room temperature, the ethanol is then distilled off under reduced pressure, the mixture diluted with water and the oxime is extracted with ethyl acetate. After drying over sodium sulphate and evaporation under reduced pressure, 9.4 g of crude base (~100% theory) is obtained. For conversion to the hydrochloride the base is dissolved in dry ethyl acetate and mixed, with stirring and thorough cooling, dropwise with 0.03 mol of ethanolic hydrochloric acid. Further purification of the filtered product is generally not required, but can be optionally effected by recrystallising from a mixture of ethanol and diethyl ether. 8.4 g of the compound of formula

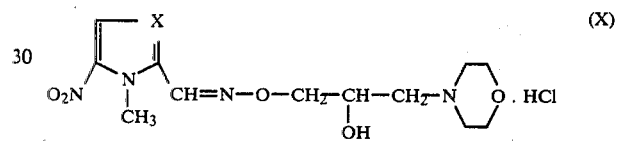

(89.4% of theory), melting point 195°–196° C. (with decomposition), are obtained in this way.

$C_{12}H_{20}ClN_5O_5$ (M.W. = 349.8)

Analysis: Calculated: C 41.21%; H 5.76%; Cl 10.14%; N 20.02%. Found: C 41.04%; H 5.81%; Cl 9.78%; N 20.01%.

This compound can also be obtained by process b) by aminolysis of 0-(2,3-epoxypropyl)-1-methyl-5-nitro-2-imidazolaldoxime with morpholine.

EXAMPLE 2

0-[3-(4-morpholinyl)-2-hydroxypropyl]-5-nitro-2-furanaldoxime hydrochloride (of formula XI) by process (a)

7.06 g (0.05 mol) of 2-formyl-5-nitrofuran are dissolved at room temperature in 80 ml of ethanol, mixed with 12.46 g (0.05 mol) 0-[3-(4-morpholinyl)-2-hydroxypropyl]-hydroxylamine dihydrochloride in 25 ml of water and subsequently a solution of 5.3 g (0.05 mol) of soda in 25 ml of water is added dropwise with stirring at room temperature. The mixture is stirred for 5 hours at room temperature and the ethanol is then distilled off under reduced pressure. The mixture is diluted with water to approximately 120 ml and the oxime is extracted with ethyl acetate. After drying over sodium sulphate and evaporation under reduced pressure, 15 g of crude base (~100% of theory) is obtained, which after dissolving in dry ethyl acetate can be converted into the crystalline hydrochloride by the dropwise addition with stirring and ice-cooling of approximately 0.05 mol of ethanolic hydrochloric acid. If desired, it can be re-crystallised from ethanol/diethyl ether. In this way, 15.5 g of the compound of formula

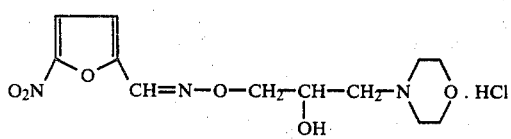 (XI)

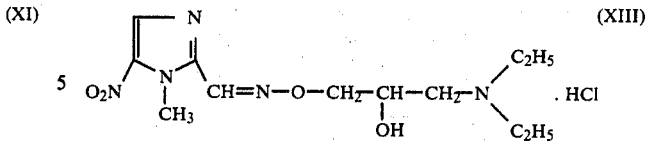 (XIII)

are obtained (92.2% of theory), melting point 182°–183° C. (with decomposition).

$C_{12}H_{18}ClN_3O_6$ (M.W. = 335.7).

Analysis: Calculated: C 42.93%; H 5.40%; Cl 10.56%; N 12.52%. Found: C 42.74%; H 5.49%; Cl 10.51%; N 12.60%.

This compound can also be prepared by process (b) by reacting 0-(2,3-epoxypropyl)-5-nitro-2-furanaldoxime with morpholine.

EXAMPLE 3

0-(3-Diethylamino-2-hydroxypropyl)-1-methyl-5-nitro-2-imidazolaldoxime hydrochloride (of formula XIII) by process (b)

First Stage: 0-(2,3-epoxypropyl)-1-methyl-5-nitro-2-imidazolaldoxime (of formula XII)

17.0 g (0.1 mol) of 1-methyl-5-nitro-2-imidazolaldoxime are added to a solution of 2.3 g (0.1 gram atom) of sodium in 300 ml of dry ethanol with stirring. A clear solution is obtained from which the solvent is evaporated in vacuo; the sodium oximate is obtained as a solid. The dry salt is suspended in 120 ml (1.5 mol) epichlorohydrin and heated under reflux. The reaction, which can be followed by thin-layer chromatography, is complete after approximately 1 hour. The resulting mixture is diluted with chloroform, precipitated sodium chloride filtered off and the filtrate is evaporated in vacuo. 19.5 g (86.3%) of crude product are obtained, from which 14.7 g of analytically pure, oily aldoxime of formula

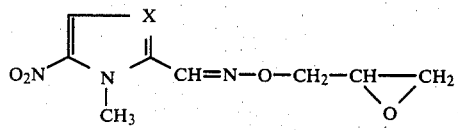 (XII)

(65% of theory) can be extracted with approximately 250 ml of boiling hot petroleum ether.

$C_8H_{10}N_4O_4$ (M.W. = 226.2)

Analysis: Calculated: C 42.48%; H 4.45%; N 24.76%. Found: C 42.15%; H 4.28%; N 24.74%.

Second Stage: Aminolysis of the epoxide with diethylamine.

2.26 g (0.01 mol) of the compound of formula XII and 0.73 g (0.01 mol) of diethylamine are heated in 20 ml of n-propanol for 4 hours with stirring and reflux. The solvent is then distilled off under reduced pressure and the residue is mixed with ethanolic hydrochloric acid (0.01 mol). By the careful addition of a little diethyl ether at boiling temperature, 1.3 g of 0-(3-diethylamino-2-hydroxypropyl)-1-methyl-5-nitro-2-imidazolaldoxime hydrochloride of formula (38.7% of theory) are crystallised out, melting point 210° C.

$C_{12}H_{22}ClN_5O_4$ (M.W. = 335.8)

Analysis: Calculated: C 42.92%; H 6.60%; Cl 10.56%; N 20.86%. Found: C 42.69%; H 6.57%; Cl 10.57%; N 20.74%.

The same compound is obtained by reacting equimolar quantities of 2-formyl-1-methyl-5-nitroimidazole and 0-(3-diethylamino-2-hydroxypropyl)-hydroxylamine dihydrochloride according to process (a) with a yield of 78%.

The following compounds are prepared analogously to the foregoing Examples by processes (a) and (b):

(4) 0-[3-(1-piperidyl)-2-hydroxypropyl]-1-methyl-5-nitro-2-imidazolaldoxime hydrochloride; melting point 170° C.

(5) 0-(3-tert.butylamino-2-hydroxypropyl)-1-methyl-5-nitro-2-imidazolaldoxime hydrochloride; melting point 218°–220° C.

(6) 0-(3-tert.butylamino-2-hydroxypropyl)-5-nitro-2-furanaldoxime hydrochloride; melting point 178°–179° C.

(7) 0-(3-di-n-butylamino-2-hydroxypropyl)-1-methyl-5-nitro-2-imidazolaldoxime hydrochloride; melting point 103° C.

(8) 0-(3-diethanolamino-2-hydroxypropyl)-1-methyl-5-nitro-2-imidazolaldoxime hydrochloride; melting point 145°–146° C.

(9) 0-(3-diethanolamino-2-hydroxypropyl)-5-nitro-2-furanaldoxime hydrochloride; melting point 155°–156° C.

(10) 0-[3-(N-methyl-N-phenylamino)-2-hydroxypropyl]-1-methyl-5-nitro-2-imidazolaldoxime hydrochloride; melting point 171°–172° C.

(11) 0-[3-(N-methyl-N-phenylamino)-2-hydroxypropyl]-5-nitro-2-furanaldoxime hydrochloride; melting point 152°–154° C. (with decomposition).

(12) 0-[3-(1-pyrrolidinyl)-2-hydroxypropyl]-1-methyl-5-nitro-2-imidazolaldoxime hydrochloride; melting point 190°–191° C.

(13) 0-(3-hexamethyleneimino-2-hydroxypropyl)-1-methyl-5-nitro-2-imidazolaldoxime hydrochloride; melting point 170° C.

(14) 0-(3-hexamethyleneimino-2-hydroxypropyl)-5-nitro-2-furanaldoxime hydrochloride; melting point 154°–156° C.

(15) 0-[3-(2,5-dimethyl-1-pyrrolidinyl)-2-hydroxypropyl]-1-methyl-5-nitro-2-imidazolaldoxime hydrochloride; melting point 200°–202° C.

(16) 0-[3-(2,6-dimethyl-1-piperidyl)-2-hydroxypropyl]-1-methyl-5-nitro-2-imidazolaldoxime hydrochloride; melting point 220° C.

(17) 0-[3-(2,6-dimethyl-1-piperidyl)-2-hydroxypropyl]-5-nitro-2-furanaldoxime hydrochloride; melting point 180°–181° C.

(18) 0-[3-(2,2,6,6-tetramethyl-1-piperidyl)-2-hydroxypropyl]-1-methyl-5-nitro-2-imidazolaldoxime hydrochloride; melting point 186° C.

(19) 0-[3-(4-methyl-1-piperazinyl)-2-hydroxypropyl]-1-methyl-5-nitro-2-imidazolaldoxime dihydrochloride; melting point 230° C. (with decomposition)

(20) 0-[3-(4-β-hydroxyethyl-1-piperazinyl)-2-hydroxypropyl]-1-methyl-5-nitro-2-imidazolaldoxime dihydrochloride; melting point 190° C.

(21) 0-[3-(4-β-hydroxyethyl-1-piperazinyl)-2-hydroxypropyl]-5-nitro-2-furanaldoxime dihydrochloride; melting point 207°–210° C. (with decomposition)

(22) 0-[3-(4-phenyl-1-piperazinyl)-2-hydroxypropyl]-1-methyl-5-nitro-2-imidazolaldoxime monohydrochloride; melting point 183° C. (with decomposition)

(23) 0-(3-diethylamino-2-hydroxypropyl)-5-nitro-2-furanaldoxime hydrochloride; melting point 150°–151° C.

The synthesis of the basically substituted 0-(2-hydroxypropyl)-hydroxylamines of formula III used as starting compounds in process (a) is described in our copending patent application Ser. No. 850,057, filed Nov. 9, 1977 (corresponding to German Application No. P 26 51 083.8). Other starting compounds are known per se.

It is not intended that the examples given herein should be construed to limit the invention thereto, but rather thay are submitted to illustrate some of the specific embodiments of the invention. Resort may be had to various modifications and variations of the present invention without departing from the spirit of the discovery or the scope of the appended claims.

What we claim is:

1. Compounds of general formula

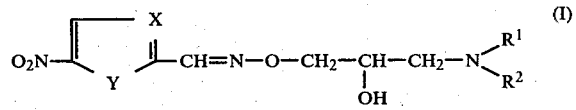

wherein X represents a methine group and Y is an oxygen atom, or X represents a nitrogen atom and Y the group NR³ in which R³ represents a radical selected from the group consisting of a hydrogen atom, a methyl, ethyl and hydroxethyl group; and R¹ and R² each represent a radical of the group hydrogen atom, an alkyl and hydroxyalkyl group each containing up to 6 carbon atoms, or a phenyl or naphthyl group; and R¹ and R², together with the nitrogen atom to which they are attached, form a 5- to 7-membered saturated ring or a piperazine, homopiperazine, morpholine or thiamorpholinyl ring, which rings are unsubstituted or substituted by at least one of the groups an alkyl and hydroxyalkyl group each containing up to 6 carbon atoms and a phenyl group which may be substituted by one or several alkyl groups which together with the phenyl group consist of not more than 10 carbon atoms, and physiologically acceptable acid addition salts thereof.

2. Compounds as claimed in claim 1 wherein R¹ and R² together with the nitrogen atom to which they are attached form a ring in which any substituents on the ring contain a total of not more than 12 carbon atoms.

3. Compounds as claimed in claim 1 or 2 wherein R¹ and R² together contain a total of from 4 to 10 carbon atoms.

4. Compounds of general formula

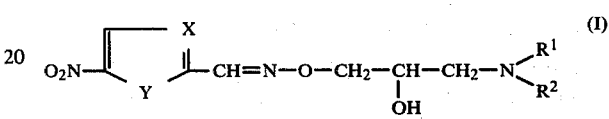

wherein X represents a methine group and Y is an oxygen atom, or X represents a nitrogen atom and Y the group NR³ in which R³ represents a radical selected from the group consisting of a hydrogen atom, a methyl, ethyl and hydroxyethyl group; and wherein R¹ and R² together with the nitrogen atom to which they are attached, represent a radical selected from the group consisting of hexamethyleneimine, 2,5-dimethylpyrrolidinyl, 2,6-dimethylpiperidyl and morpholinyl.

5. A pharmaceutical composition for the treatment of protozoic diseases comprising as active ingredient at least one compound of formula I as defined in claim 1 or a physiologically acceptable acid addition salt thereof in combination with a pharmaceutical carrier or excipient containing at least 100 mg of said active ingredient per dosage unit.

6. A pharmaceutical composition for the treatment of protozic diseases comprising as active ingredient at least one compound of Formula I as defined in claim 1 or a physiologically acceptable acid addition salt thereof in combination with a pharmaceutical carrier or excipient wherein each dosage unit comprises 1,000 to 2,000 mg of the active ingredient.

* * * * *